United States Patent [19]

Mitchell

[11] 4,186,594
[45] Feb. 5, 1980

[54] PORTABLE SPRING TESTER

[76] Inventor: William E. Mitchell, 800 Tanglewood Rd., West Islip, N.Y. 11795

[21] Appl. No.: 946,505

[22] Filed: Sep. 28, 1978

[51] Int. Cl.² .................. G01M 13/00; G01L 1/04
[52] U.S. Cl. ................................. 73/118; 73/161
[58] Field of Search ..................... 73/161, 790, 118

[56] References Cited
U.S. PATENT DOCUMENTS

| | | | |
|---|---|---|---|
| 2,340,277 | 1/1944 | Sturtevant | 73/161 |
| 2,518,408 | 8/1950 | Weyand | 73/161 X |
| 3,640,129 | 2/1972 | Bandimore | 73/161 X |

*Primary Examiner*—Daniel M. Yasich

*Attorney, Agent, or Firm*—Kane, Dalsimer, Kane, Sullivan & Kurucz

[57] ABSTRACT

A portable spring tester adapted for use in testing spring strength for spring assemblies mounted on automobiles and the like. The tester includes a mounting arm for coupling and removably locating the tester in fixed position on the spring assembly. An actuating arm extends from the mounting arm in position to engage with the spring assembly and be shiftable to bias the spring. Engagement surfaces are on the tester for removably mounting a strength indicator thereon so that when the actuating arm is shifted to bias the spring the strength indicator will provide a reading to indicate the spring strength.

4 Claims, 4 Drawing Figures

PORTABLE SPRING TESTER

BACKGROUND OF THE INVENTION

Traditionally in the automotive field as well as in similar mechanical environments, it has been found to be necessary for many reasons to test spring strengths. This is done for purposes such as checking for normal wear and tear for possible replacement of springs and, in certain environments, legal requirements necessitate that springs be tested at various frequencies to determine their capabilities. This is often done for safety reasons.

Conventionally, the springs are tested by removing them from their assemblies mounted in the larger structure such as an automobile engine, and placing them on a laboratory testing device. Each individual spring is tested in this manner. This is naturally an inefficient and time consuming procedure. Additionally, this can be very expensive since conventional type of laboratory testing devices are costly. An example is the spring tester manufactured by ACE (Atlantic Coast Engineering) of Monrovia, Md. The testers manufactured by that company are conventional standard testers in industry, such as the racing industry, and are used by both the NHRA and IHRA to check springs for legality. These devices are quite large and bulky and expensive. In general the testers are designed to test spring strength up to conventional limits such as 500-1000 pounds.

In dealing with complex and large automotive structures and similar types of machinery where many springs are employed particularly in valve type assemblies, it is naturally quite inconvenient and time consuming to have to remove each spring and take it to a laboratory for testing purposes. Accordingly, it would be very advantageous to be able to test each spring as it is mounted in position on the machinery by use of a light weight portable testing device that gives an immediate strength reading for each individual spring. A light weight inexpensive device which would achieve this purpose would be a considerable improvement over the costly laboratory devices presently in use.

SUMMARY OF THE INVENTION

With the above background in mind, it is among the primary objectives of the present invention to provide a portable light weight inexpensive spring tester which can be easily and efficiently removably mounted on a piece of machinery such as a portion of an automobile engine to test spring strength. It is particularly useful with valve springs and can be easily coupled with the spring assembly and shifted to bias the spring and provide an immediate readout of spring strength. In this manner, the device can be used to quickly and efficiently test spring strength for wear and tear and legality purposes. The tester can be coupled with each spring assembly in quick and efficient fashion in sequence without having to dismount or diassemble any of the machinery structure particularly the valve assembly.

The tester is manufactured of a single one piece inexpensive lightweight material, such as a conventional metal as steel or aluminum. It can be conveniently carried and used with a conventional type of torque wrench to provide a direct readout of spring strength in pounds. The tester is small and compact lending itself to portability and ease of coupling and uncoupling with spring assemblies such as automobile valve assemblies. Positive means is provided to prevent slippage of the tester when mounted and to facilitate its movement in biasing the spring to provide the direct strength readout.

The lightweight simple one piece design of a compact nature permits its use easily in difficult access locations such as underneath an automobile hood, particularly in a racing vehicle. This becomes particularly advantageous where down time must be kept in a minimum and the engine must be kept in operating condition over the greatest percentage of time. In racing vehicles, this is of extreme importance where the engine must be kept in operable assembled condition for the greatest percentage of usable time.

With the present device quick and repeated checks of valve spring strength can be carried out at rapid and frequent times without detracting from other mechanical operations being conducted on the piece of machinery such as a racing engine.

In summary, a portable spring tester adapted for use in testing spring strength for spring assemblies mounted on automobiles and the like is provided. The tester includes a mounting arm with coupling means thereon for removably locating the tester in fixed position on the spring assembly. An actuating arm extends from the mounting arm in position to engage with the spring assembly and be shiftable to bias the spring. Engagement means is on the tester for removably mounting a strength indicator thereon so that when the actuating arm is shifted to bias the spring, the strength indicator will provide a reading to indicate the spring strength.

With the above objectives among others in mind, reference is made to the attached drawing.

DETAILED DESCRIPTION

Figure 1:
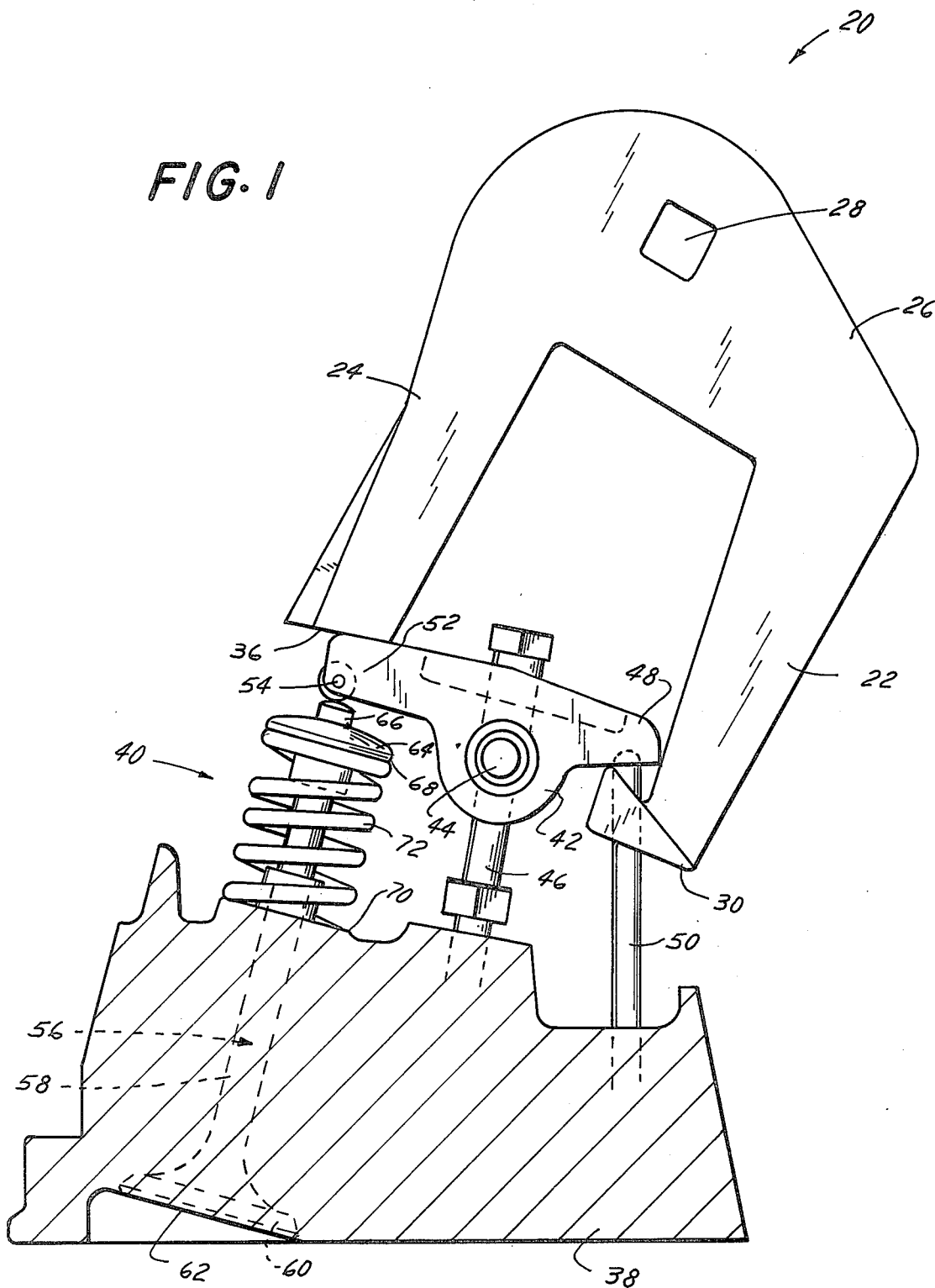
FIG. 1 is a side elevation view of the portable spring tester of the invention coupled with a valve spring assembly of an automobile engine.

Portable spring tester 20 is formed of one piece of high strength material such as spring steel or aluminum. It is U-shaped in configuration and includes a mounting arm 22 and actuating arm 24 integrally formed with a central base portion 26.

The tester is relatively thin in cross section and has a hole 28 extending through the base portion. The location of hole 28 is a matter of choice depending upon the type of strength indicator used with the tester and the type of spring assembly to which the tester is to be removably coupled. For similar reasons, the configuration of the hole 28 is a matter of choice and for use with a conventional type of torque wrench, it has been found effective to use a square opening as shown in the embodiment of the drawings. Engagement with a square lug of a torque wrench by the square hole in the tester will coordinate rotational movement of the torque wrench with rotational movement of the tester 20. Relative movement therebetween is eliminated.

Naturally, when other common type of strength indicators are to be used instead of the torque wrench in the depicted embodiment, appropriate engagement surfaces can be provided on tester 20 in place of hole 28 to accomplish the coupling action and to prevent relative rotation therebetween.

The free end 30 of arm 22 is formed with an inwardly extending pair of tangs 32 and 34 which are substantially parallel and spaced from one another to capture a portion of the spring assembly therebetween. The tangs are angled inwardly and upwardly from the free end 30 of arm 22 to facilitate their interengagement with a portion of the spring assembly.

Actuator arm 24 has a flat free end surface 36 for engagement with the spring assembly and facilitate application of a depressing force to bias the spring of the assembly. The relative parameters and dimensions of the arms 22 and 24 and the base portion 26 along with the location of the opening 28 is a matter of choice depending upon the size and type of spring assembly for which the tester is designed. This is also true in regard to the shape and configuration of the spaced tangs 32 and 34 on the free end 30 of the mounting arm 22.

In the depicted embodiment, the portable spring tester 20 is shown for use in a conventional type of automobile engine, such as a racing engine. The engine includes a rigid non-movable supporting structure 38 on which are mounted a plurality of valve spring assemblies of a conventional nature such as assembly 40 shown in the depicted embodiment. Assembly 40 includes a rocker arm 42 pivotally mounted about a mounting pin 44 coupled to a fixed central post 46. The post 46 is mounted in fixed position on the engine structure 38. The rocker arm 42 is pivotally mounted about its central portion and has a one end 48 attached to a reciprocal rod 50 journaled in engine structure 48. The opposing end 52 of the rocker arm 42 is pivotally affixed by pin 54 to a valve member 56.

The valve member 56 includes a valve stem 58 terminating at one end in a valve head 60 normally resting on a valve seat 62. The other end of the valve stem has a cap 64 mounted adjacent to the tip 66. The undersurface 68 of the cap and an opposing fixed surface 70 on motor 38 form surfaces to capture a helical valve spring 72 therebetween. The valve spring 72 surrounds the stem 58 of valve member 56.

Figure 2:
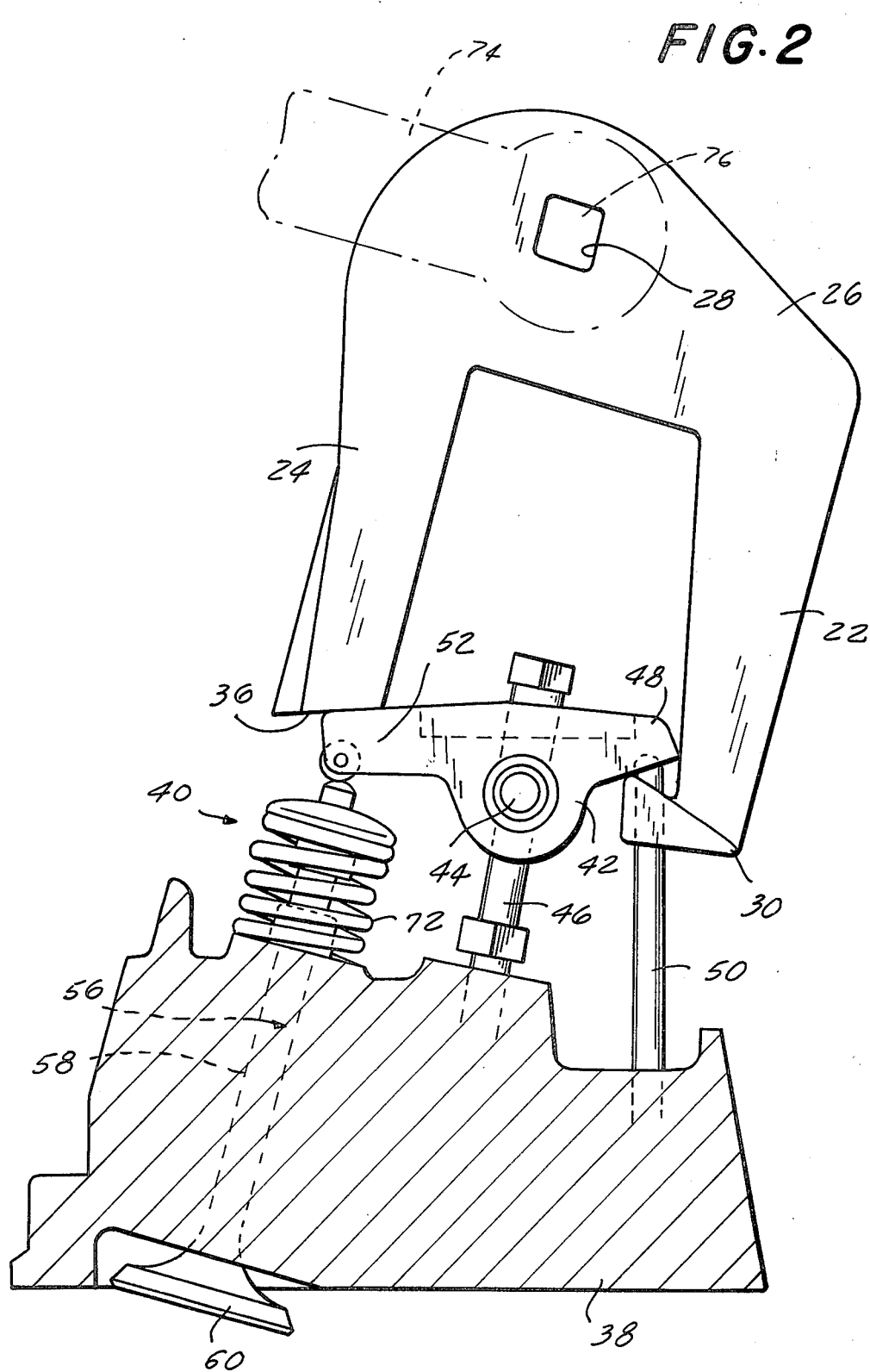
FIG. 2 is a side elevation view thereof with the spring tester having been shifted to a reading position by coupling and movement of a torque wrench, a fragmentary portion of which is shown in dot lines.
Figure 3:
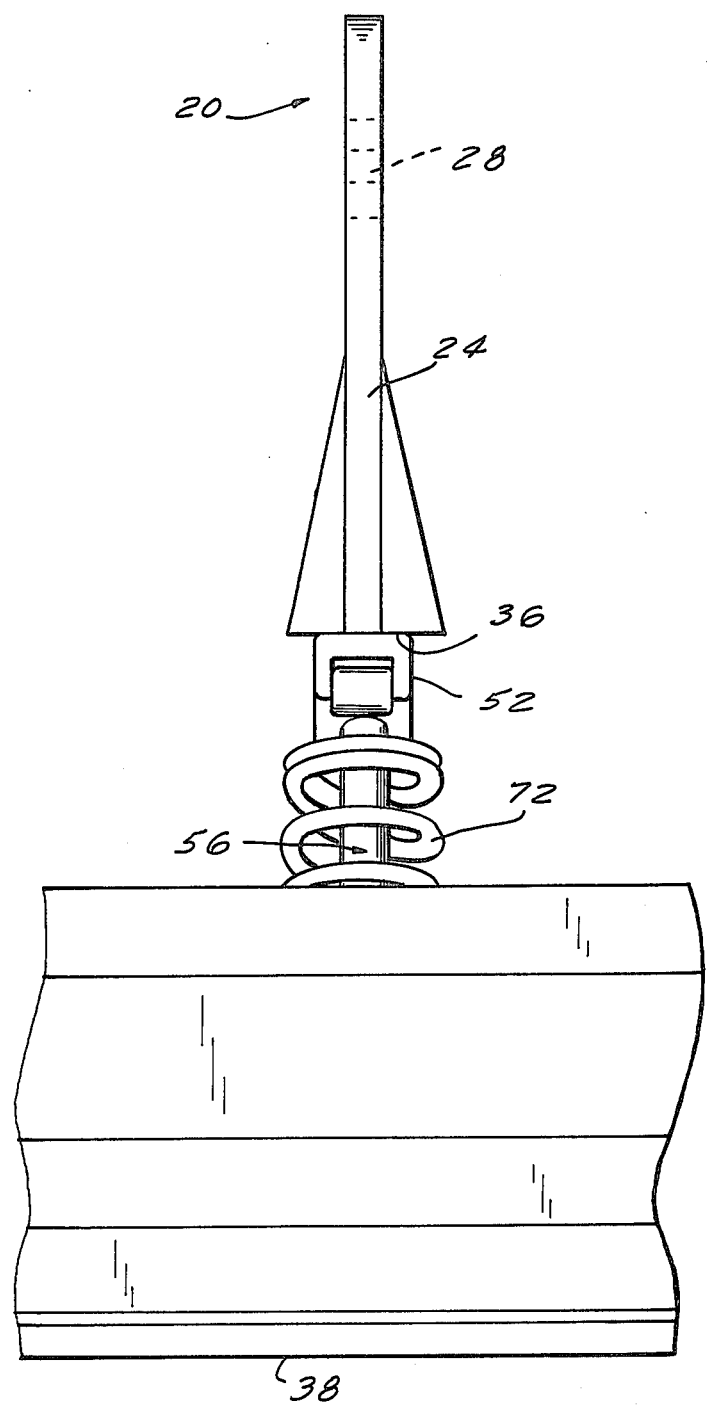
FIG. 3 is a front elevation view of the portable spring tester in the position of FIG. 1.
Figure 4:
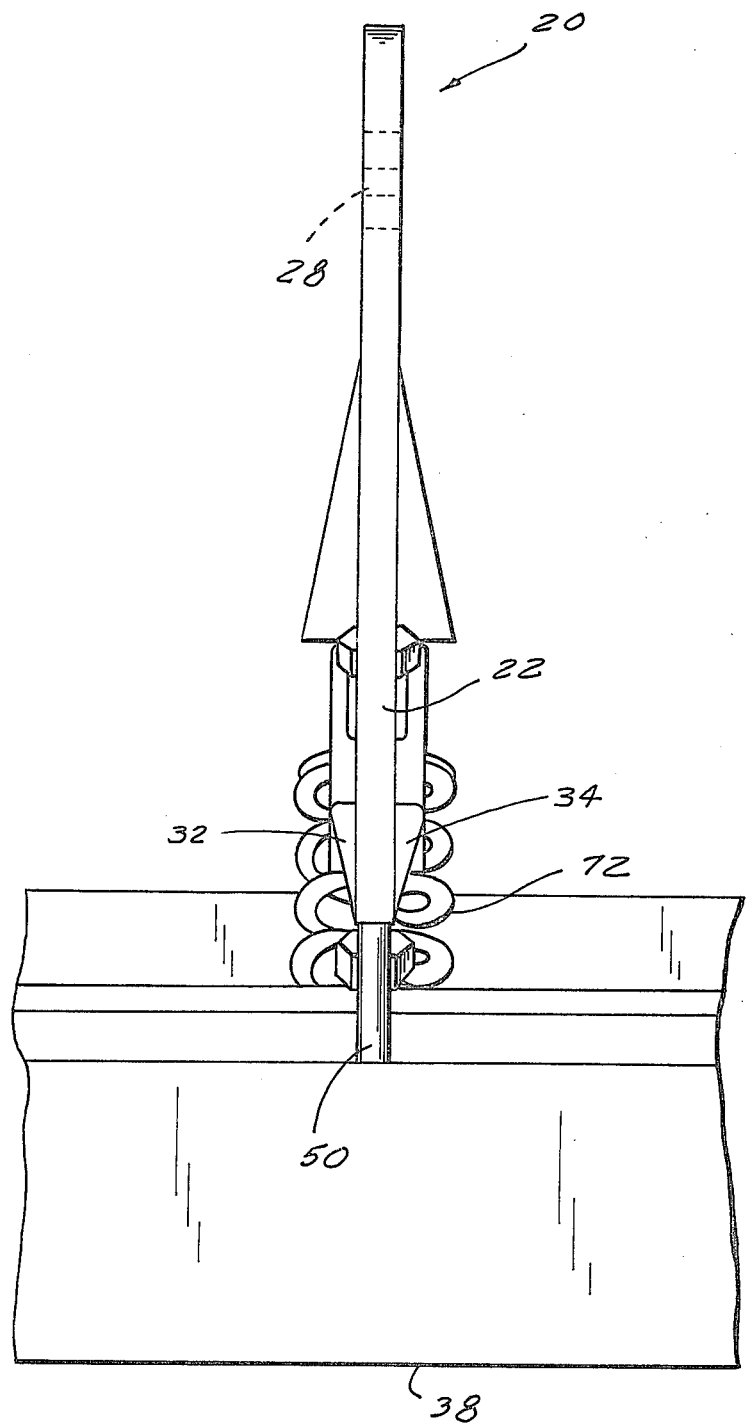
FIG. 4 is a rear elevation view thereof in the position shown in FIG. 1.

End portion 52 of the rocker arm is in engagement with the tip 66 of valve stem 58. Thus, when the rocker arm is pivoted in one direction it will force the valve member 56 to shift and unseat valve head 60 from valve seat 62. This action biases helical spring 72 so that when the rocker arm is released the spring will return the valve member to the closed position. The valve in FIGS. 1, 3 and 4 is depicted in the closed position. It is shown in the open position in FIG. 2 while it is being tested by spring tester 20.

To accomplish the testing action, spring tester 20 is quickly and easily located in the position as shown in the drawings. Flange tangs 32 and 34 engage with the undersurface of end portion 48 of the rocker arm 42 and surround reciprocal rod 50. The end portion 48 of the rocker arm also engages with a point on the inner surface of mounting arm 22. The configuration of spring tester 20 is such that in this position actuator arm 24 will have its flat free end 36 in engagement with the top of the other end portion 52 of rocker arm 42. This mounting procedure can be accomplished in a quick and efficient manner as can be readily envisioned.

A common type of torque wrench 74 having a gauge (not shown) which provides a direct readout in pounds for spring strength is removably mounted on the tester. One end of the torque wrench has a square lug 76 which fits in square hole 28 in tester 20. The engagement between the square sides of the hole and the lug prevent relative rotation between the torque wrench and the tester. Thus, when the torque wrench is rotated the tester will be correspondingly moved so that actuator arm 24 is moved downward depressing rocker arm portion 52 and accordingly valve stem 58. This opens the valve and biases helical spring 72 into the position of FIG. 2. The strength of the spring is measured by a direct readout in pounds on the gauge on the torque wrench 74. In this manner, the spring strength is tested without the necessity of having to disassemble the valve spring assembly mounted on the motor.

The wrench and the tester can then be easily removed from one another and from engagement with the rocker arm and shifted to a further spring assembly for testing purposes. Thus, the testor is portable and can be easily and efficiently and quickly used with mechanism such as valve assemblies on automobiles to test the springs thereon.

Thus the several aforenoted objects and advantages are most effectively attained. Although several somewhat preferred embodiments have been disclosed and described in detail herein, it should be understood that this invention is no sense limited thereby and its scope is to be determined by that of the appended claims.

I claim:

1. A portable spring tester adapted for use in testing spring strength for spring assemblies mounted on automobiles and the like comprising; a mounting arm with means thereon for removably locating the tester in fixed position on supporting structures on the spring assembly, an actuating arm extending from the mounting arm in position to engage with the spring assembly and be shiftable to bias the spring, engagement means on the tester for removably mounting a strength indicator thereon so that when the actuating arm is shifted to bias the spring, the strength indicator will provide a reading to indicate the spring strength, the mounting arm and the actuating arm are integrally formed with a central base portion into a U-shaped configuration with each arm forming an opposing leg of the U-shaped tester, the means for removably locating the tester in fixed position on supporting structures being on an edge of the mounting arm distal from an inner section of the central base portion, and the end of the actuating arm distal from the central base portion being substantially axially aligned with the spring to form an engagement surface with the spring assembly which acts in substantially a direct axial direction to bias the spring and thereby facilitate operation of the tester and to facilitate the provision of an accurate reading to indicate spring strength, the means for removably locating the tester in fixed position on supporting structures on the spring assembly including a laterally extending flange on an end of the mounting arm formed by two parallel tangs, and the tangs being positioned to capture a reciprocal rod means on said spring assembly therebetween with the upper surface of the tangs bearing on an adjacent portion of the rod means to thereby removably mount the tester in position on the spring assembly.

2. The invention in accordance with claim 1 wherein the engagement means is a hole on the tester in position to receive and engage with a portion of a strength indicator and the hole is square shaped in configuration, and the strength indicator is a torque wrench with a gripping portion extending therefrom and a gauge portion thereon so that when the torque wrench grips and actuates the tester to bias the spring, the gauge on the wrench will provide a direct reading of the spring strength.

3. The invention in accordance with claim 1 wherein the portable spring tester is formed of one piece of light weight high strength metal material.

4. The invention in accordance with claim 1 wherein the spring assembly is of the valve type including a substantially horizontal rocker arm pivotally mounted to a fixed support intermediate its ends, one end of the rocker arm mounted to a reciprocally movable valve stem, a helical spring captured on the valve stem between a portion thereof and the supporting surface so that reciprocation of the valve stem in one direction will bias the spring and release thereof will permit the biased spring to return the valve stem in the opposite direction, and the valve type spring assembly being adapted to be mounted on an automobile engine.

* * * * *